United States Patent [19]

Pagden

[11] Patent Number: 4,781,193

[45] Date of Patent: Nov. 1, 1988

[54] HEADACHE TREATMENT APPARATUS

[76] Inventor: Kenneth L. Pagden, P.O. Box 581, Leeton, Australia, 2705

[21] Appl. No.: 391,187

[22] Filed: Jun. 23, 1982

[30] Foreign Application Priority Data

Mar. 7, 1982 [AU] Australia .............................. 85508/82

[51] Int. Cl.$^4$ ............................................... A61F 7/00
[52] U.S. Cl. .................................................... 128/402
[58] Field of Search ................................ 128/399–403, 128/303.1; 604/20

[56] References Cited

U.S. PATENT DOCUMENTS

| | | | |
|---|---|---|---|
| 1,710,882 | 4/1929 | Larson | 128/402 |
| 1,964,655 | 6/1934 | Williamson | 128/402 |
| 2,038,275 | 4/1936 | Fogg | 128/402 |
| 3,463,161 | 8/1969 | Ardrassy | 128/403 |
| 3,823,575 | 7/1974 | Parel | 128/303.1 |
| 3,889,101 | 1/1975 | Woods | 128/399 |
| 4,154,245 | 5/1979 | Daily | 128/400 |
| 4,170,998 | 10/1979 | Sauder | 128/400 |
| 4,280,499 | 1/1981 | Sguazzi | 128/303.1 |
| 4,382,446 | 5/1983 | Truelock et al. | 128/402 |
| 4,425,917 | 1/1984 | Kuznetz | 128/399 |

Primary Examiner—Max Hindenburg
Attorney, Agent, or Firm—Beveridge, DeGrandi & Weilacher

[57] ABSTRACT

A headache treatment apparatus which simultaneously heats and cools different portions of a patient's head including a cap containing a heating element to heat the top of the patient's head above its normal temperature. A head-band is spaced from and depends from the cap and encircles a zone of the patient's head which includes the patient's brow and temples. The head-band contains a cooling coil through which a cooling fluid circulates to cool the encircled zone below its normal temperature.

4 Claims, 1 Drawing Sheet

HEADACHE TREATMENT APPARATUS

BACKGROUND OF THE INVENTION

The object of this invention is to provide simple but effective means for the relief or cure of headache whether it be the common headache, migraine or other head pain or discomfort.

The invention depends on the principle, which I have extensively tested by experiment, that headache is banished or markedly relieved if two certain specific areas of the head are respectively and simultaneously heated above normal temperature in the case of one area and cooled below that temperature in the case of the other.

My experiments have shown that to be effective heat has to be applied to the top or crown area of the head at the same time while a lower area or zone of the head is cooled. This zone is below and spaced from the crown area; being a zone, just above the ears, which includes the brow and temples.

SUMMARY OF THE INVENTION

The invention provides headache treatment apparatus comprising:

a cap which covers the top of a patient's head, a heating element contained in said cap, means to energize said heating element thereby to heat the top of a patient's head above its normal temperature, a head-band dependent and spaced from said cap; which when said cap is on top of the patient's head, encircles a zone of the patient's head which includes his brow and temples, a cooling coil contained in said headband, and means to circulate a cooling fluid through said coil thereby to cool said zone below its normal temperature.

DESCRIPTION OF THE DRAWING

An example of the invention is illustrated in the drawings herewith.

DESCRIPTION OF THE INVENTION

Figure 1:
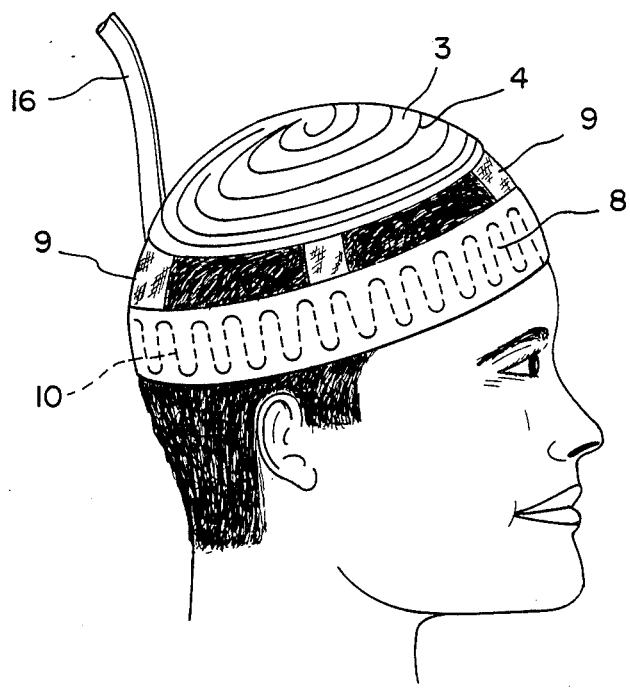
FIG. 1 is a perspective view of the treatment headgear applied to a patient.

Referring to the drawings, a cranial cap 3 houses a heating element 4 in much the same way as applies in an artificially warmed blanket.

Figure 2:
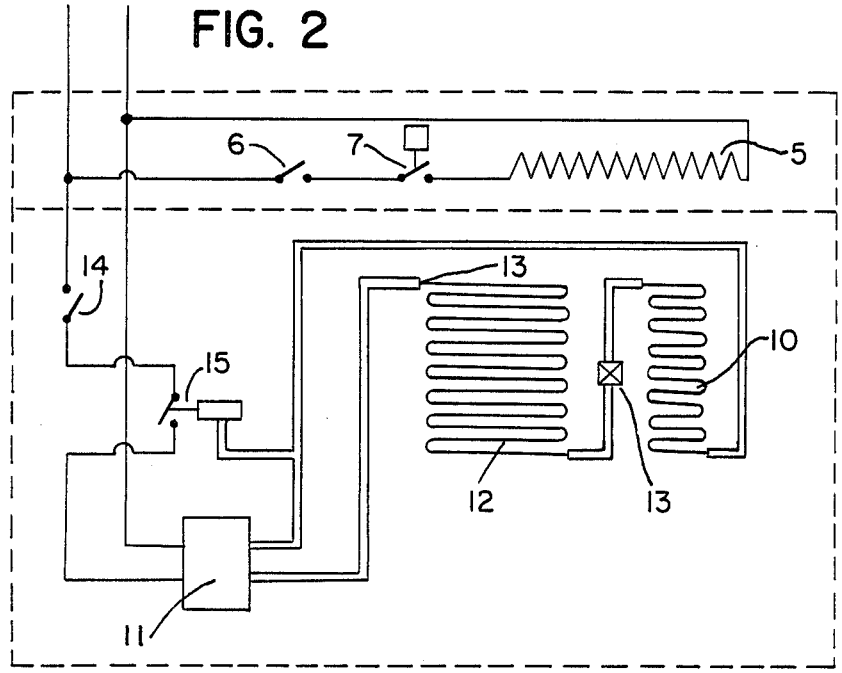
FIG. 2 is a diagram of conventional heating and cooling means of a kind suited to the purposes of the present invention.

Element 4 may be tubular and the means to energize it may consist of apparatus to circulate a hot gas or liquid through it. For preference, however, element 4 is an electrical resistance coil as indicated at 5 in FIG. 2. Coil 5 is circuited in conventional manner (also as indicated in FIG. 2) its circuit preferably including an on-off switch 6 and a thermostatically controlled switch 7 by which a selected treatment temperature may be established.

Both dependent and spaced from cap 3 is a head-band 8 designed to encircle a zone of the patient's head which includes the brow and temples. Head-band 8 is suspended from cap 3 by thongs 9. These may be straps which are length adjustable, (by provision of buckles, sliding clasps, or the like) so that the head-gear may be suited to differently sized heads.

Head-band 8 houses a cooling coil 10 furnished with means to circulate a cooling fluid through it. These means preferably comprise a conventional refrigeration cycle (as indicated in FIG. 2) incorporating compressor 11, condenser 12, expansion valve 13, on-off switch 14 and control thermostat 15.

Supply lines for element 4 and coil 10 are indicated at 16.

I claim:

1. Headache treatment apparatus comprising:

a cap which covers the top of a patient's head, a heating element contained in said cap, means to energize said heating element thereby to heat the top of a patient's head above its normal temperature, suspension means extending from said cap and supporting a head-band spaced below said cap, whereby when said cap is on top of the patient's head, said head-band encircles a zone of the patient's head which includes his brow and temples, a cooling coil contained in said headband, and means to circulate a cooling fluid through said coil thereby to cool said zone below its normal temperature.

2. Apparatus according to claim 1 wherein said heating element is an electrical resistance.

3. Apparatus according to claim 1 wherein said headband is suspended from said cap by length-adjustable straps.

4. Apparatus according to claim 2 wherein said headband is suspended from said cap by length-adjustable straps.

* * * * *